United States Patent [19]

Lassen et al.

[11] 4,442,113

[45] Apr. 10, 1984

[54] LONG-TERM WEIGHT REDUCTION OF OBESE PATIENTS USING FEMOXETINE

[75] Inventors: Joergen B. Lassen, Glostrup; Birte K. Skrumsager, Broenshoej; Joergen A. Christensen, Virum, all of Denmark

[73] Assignee: A/S Ferrosan, Soborg, Denmark

[21] Appl. No.: 261,479

[22] Filed: May 7, 1981

[51] Int. Cl.³ .......................................... A61K 31/445
[52] U.S. Cl. ..................................................... 424/267
[58] Field of Search ........................................ 424/267

[56] References Cited

U.S. PATENT DOCUMENTS 3,912,743 10/1975 Christensen et al. ............... 424/267

OTHER PUBLICATIONS

International J. of Obesity 1, pp. 15–42 (1977)—J. E. Blundell.
Central Mechanisms of Ansr.-Drugs, pp. 83–109 (1978)—Garattin et al. or Blundell et al.
Life Sciences 28, 77–82, (1981)—Hoebel et al.
Drugs 10(4), 241—328 (1975)–Pinder et al.
Alimentayinne Metabolism Nutrizione 1, 383 (1980), Wollesen et al.
European J. of Pharm. 32, 108–115 (1975)—Lassen et al.
Psychopharmacologia 42, 21–26 (1975)—Lassen et al.
J. Chromatogr. 133, 147–152 (1977)—Bechgaard et al.
Analytica Chimica Acta, 99, 189–192 (1978)—Bechgaard et al.
J. Neurochemistry 24, 47–50 (1975)—Squires.
Lancet 1, 503–505 (1973)—Stunkard et al.
Brit. J. of Psg. 123, 501–507 (1973)—Paykel et al.
J. Pharm. Pharmac. 28, 318–320 (1976)—Goudie et al.
Arzneim-Forsch (Drug Res.) 25 (11), 1758–1762 (1975)—Duhault et al.
European J. of Pharmacol. 40, 121–130 (1976)—Sugrue et al.

*Primary Examiner*—Douglas W. Robinson
*Attorney, Agent, or Firm*—Gordon W. Hueschen

[57] ABSTRACT

A method for assisting with appetite and weight control and reduction in obese human patients, which comprises the step of orally or rectally administering an appetite-suppressant compound selected from the group consisting of femoxetine and a pharmaceutically-acceptable salt thereof in an effective appetite-suppressant amount over a period of at least eight (8) weeks is disclosed. The appetite-suppresssant compound is preferably orally administered together with a pharmaceutically-acceptable carrier in a daily dosage of 100 to 1,000 mg in the form of a tablet containing about 100 to 300 mg of the appetite-suppressant compound, which is preferably a pharmaceutically-acceptable femoxetine acid addition salt, especially the hydrochloride.

16 Claims, No Drawings

LONG-TERM WEIGHT REDUCTION OF OBESE PATIENTS USING FEMOXETINE

BACKGROUND OF THE INVENTION

1. Field of Invention

Appetite and weight control or reduction in human patients; long-term treatment without the development of tolerance; employment of femoxetine and salts thereof in such method, particularly such method involving treatment of obese human patients over a period of at least eight (8) weeks.

2. Prior Art

Over the past years, numerous agents have been employed or proposed for their anorexigenic and weight control or reduction effects, particularly in obese humans. These agents have been of numerous types. Sympathomimetic amines have been employed but generally have been found to have the objectionable side effects of anxiety, restlessness, and insomnia due to their strong central nervous system stimulatory effect. Compounds of other structures have therefore been explored. Among the compounds proposed for anorexigenic drugs for the control or reduction of appetite and weight are compounds which increase the neuronal release of noradrenaline (NA) and dopamine (DA). Such compounds have been found effective, but are subject to the disadvantages that patients generally develop a tolerance to such drugs as are currently available. As a result, extended treatment is not feasible, since the anorexigenic effect tends to diminish by the eighth week of administration or earlier, with resulting termination of weight reduction and, in fact, a return to a weight gain situation from previously attained low levels despite continuation of treatment beyond the point where tolerance develops. The potential use of such products has accordingly been severely curtailed in practice, since appetite and weight control and reduction programs, especially in obese patients, are most desirably continued far beyond an eight-week treatment schedule. Of available anorexigenic drugs, only fenfluramine has appeared to have an anorexigenic and weight-reducing effect over a treatment period extending beyond eight (8) weeks. Fenfluramine is, however, recognized as being characterized by a mode of action which is different from the serotonin (5-HT) uptake-inhibitors, in fact operating by the stimulation of the release of 5-HT from storage sites rather than by blocking its uptake, so that no conclusions can be reached with regard to 5-HT uptake-inhibitors or blockers based upon the performance of the known 5-HT release-stimulating drug fenfluramine. Since fenfluramine is also releasing NA and DA, the effect on 5-HT is not selective.

Numerous efforts to provide long-acting anorexigenic drugs, to which the patient does not develop tolerance, of various types and structures, have been undertaken, but with no substantial elimination of their shortcomings. The need for additional and improved products and long-term methods for the effective control and reduction of appetite and weight, especially in obese patients, without undesirable side effects, is apparent.

The possible use of 5-HT uptake-inhibitors in modifying feeding behavior and decreasing food intake in rats is reviewed by J. E. Blundell in the "International Journal of Obesity" (1977), 1, at pages 15–42. A copy of this publication will be provided upon filing the present application. Blundell and Latham expanded the art in this field with their article entitled "Pharmacological Manipulation of Feeding Behavior: Possible Influences of Serotonin and Dopamine on Food Intake" in the book entitled *Central Mechanisms of Anorectic Drugs*, edited by S. Garattini and R. Samanin, Raven Press, New York (1978) at pages 83–109, a copy of which will also be provided. At pages 89 and 90, figures evidencing the effect of anorectic drugs on eating behavior as measured during a one-hour feeding test are provided, including the product FG 4963, which is the product femoxetine, as its hydrochloride. These authors did not suggest that femoxetine would be a valuable anorectic drug over a long-term period, much less for a period in excess of eight (8) weeks, without evidence of patient-developed tolerance or untoward side effects, or even that femoxetine would have anorectic action beyond the one-hour eating period involved in the test protocol they reported.

Of course, it is already well-established that a single dose of an anorectic drug can result in a loss of appetite and weight, but that food intake and weight quickly return to base line and are followed by overeating and weight gain with an ultimate result of excess food intake, overeating, and increase in body fat which can persist as long as two (2) months or more. This is established, for example, for amphetamine, "the prototypical drug for producing anorexia and weight loss in animals and people", Hoebel et al., Princeton University, Life Sciences Vol. 28, pp. 77–82 (1981), Pergamon Press.

Among anorectic drugs which do produce patient-developed tolerance after eight (8) weeks of treatment or earlier and which, accordingly, are not of value in such treatment beyond that point, may be mentioned the products diethylpropion, chlorphentermine, phentermine, desamphetamine, and phenmetrazine, as set forth in the review article in "Drugs", 1975, 10(4), pages 241–328, and as graphically illustrated in FIG. 3, page 271 of that article.

In the use of femoxetine as a prophylactic treatment for migraine, with treatment extending at a 400 mg daily dosage over a period of six (6) weeks, an observed side effect was reduced appetite and weight loss, but there was no suggestion that tolerance would not appear or had not appeared from the anorectic standpoint and there was no indication that such tolerance would not appear in treatment schedules extending over eight (8) weeks and beyond. Some of our results with femoxetine were also noted in a publication in "Alimentazione Metabolismo Nutrizione" (1980), 1, 383, an abstract of a paper presented at the Third International Congress on Obesity in Rome, Oct. 8–11, 1980, which was published as early as June, 1980 but which was not further elaborated upon at the conference or followed by any expanded publication. This publication is within one year of the date on which the present application will be filed.

Other publications relating to femoxetine as a potential thymoleptic include the "European Journal of Pharmacology", 32 (1975) 108–115 and "Psychopharmacologia" (Berl.) 42, 21–26 (1975), which do not mention anorexigenic activity. Finally, the basic U.S. patent covering femoxetine is U.S. Pat. No. 3,912,743, issued Oct. 14, 1975, which discloses use of femoxetine and related compounds as anti-depressant and anti-Parkinson agents.

THE ACTIVE INGREDIENT

The active ingredient of the compositions and method of the present invention is femoxetine, which is (+)trans-3-[(4-methoxyphenoxy)-methyl]-1-methyl-4-phenylpiperidine, having the formula

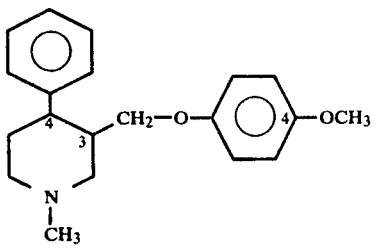

or a pharmaceutically acceptable salt thereof, such as an acid addition salt.

Physical constants of the preferred femoxetine hydrochloride salt and of the femoxetine mandelate salt are as follows:

|  | Melting Point, °C. | $[\alpha]_D^{20}$ |
| --- | --- | --- |
| Hydrochloride | 187–191 | 74–75.6° (conc. 0.05 in water) |
| Mandelate | 127.5–130 | 88–89.8° (conc. 0.05 in 96 percent ethanol) |

OBJECTS

It is an object of the present invention to provide a novel method for assisting with the control and reduction of appetite and weight, especially in obese human patients. Another object is to provide such a method which may be employed long-term without the development of anorectic tolerance to the active ingredient or anorectic drug by the patient. A further object is to provide such a method of counteracting appetite and weight and thus controlling or combating obesity without the production of undesirable central nervous system stimulation or other untoward side effects. A still further object is to provide such a method which comprises the step of orally or rectally administering to such a patient a compound selected from the group consisting of femoxetine and a pharmaceutically-acceptable salt thereof in an effective appetite-suppressant amount over a period of at least eight (8) weeks. Still another object is to provide such a method wherein the active anorexigenic compound is administered together with a pharmaceutically-acceptable carrier, preferably on a daily basis, and whereby the treatment may be continued effectively for a period in excess of eight (8) weeks and even in excess of ten (10) or twelve (12) weeks without the development of anorectic tolerance by the patient. Other objects of the invention will be apparent to one skilled in the art to which the invention pertains and still other objects will become apparent hereinafter.

The foregoing and additional objects have been accomplished by the provision of a novel method for the control or reduction of appetite and weight, especially in obese human patients, which involves the employment of femoxetine or a pharmaceutically acceptable salt thereof, which method may be effectively continued on a long-term basis without the development of anorectic tolerance by patients subjected to the treatment.

SUMMARY OF THE INVENTION

In summary, the invention comprises a method of assisting with appetite and weight control and reduction in an obese human patient which comprises the step of orally or rectally administering to the said patient an appetite-suppressant compound selected from the group consisting of femoxetine and a pharmaceutically-acceptable salt thereof in an effective appetite-suppressant amount over a period of at least eight (8) weeks; such method wherein the appetite-suppressant compound is administered together with a pharmaceutically-acceptable carrier; such method wherein the appetite-suppressant compound is administered orally in a daily dosage of about 100 to 1,000 mg; such method wherein the appetite-suppressant compound is administered orally in a daily dosage of about 400 to 600 mg; such method wherein the appetite-suppressant compound is administered orally in an oral unit dosage form containing about 100 to 300 mg thereof; such method wherein the appetite-suppressant compound is administered orally in an oral unit dosage form containing about 100 mg thereof; such method wherein the appetite-suppressant compound is administered rectally in a daily dosage of about 50 to 600 mg; such method wherein the appetite-suppressant compound is administered in the form of a rectal suppository containing about 50 to 600 mg thereof; such method wherein the appetite-suppressant compound is administered in the form of a rectal suppository containing about 300 mg of the active ingredient; such method wherein the appetite-suppressant compound is administered over a period in excess of eight (8) weeks; such method wherein the appetite-suppressant compound is administered over a period of at least twelve (12) weeks; such method wherein the appetite-suppressant compound is administered daily over a period in excess of eight (8) weeks; such method wherein the appetite-suppressant compound is administered daily over a period of at least twelve (12) weeks; particularly such method wherein the appetite-suppressant compound is a femoxetine pharmaceutically-acceptable acid addition salt which is orally-administered in a daily dosage of about 100 to 1,000 mg in the form of a tablet containing about 100 to 300 mg thereof; and especially such method wherein the compound is femoxetine hydrochloride, and remarkably such method wherein the product may be administered long term over extensive periods of eight (8) weeks and far beyond without the development of anorectic tolerance in a patient subjected to such method of treatment.

Another way of summarizing the present invention, in a preferred embodiment thereof, is as a method of assisting with appetite and weight control and reduction in an obese human patient on a long-term basis without the development of anorectic tolerance on the part of the patient which comprises the step of orally administering to the said patient an appetite-suppressant compound selected from the group consisting of femoxetine and a pharmaceutically-acceptable salt thereof in an effective appetite-suppressant amount over an extended period, the daily dosage being about 100 to 1,000 mg in a unit-dosage form containing about 100 to 300 mg thereof.

Preparation of Femoxetine and its Salts

Femoxetine and its salts are known compounds and are prepared in known manner according to the art as representatively illustrated by U.S. Pat. No. 3,912,743, issued Oct. 14, 1975, the disclosure of which is hereby incorporated by reference. In the said patent, femoxetine is representatively disclosed in the form of its hydrochloride salt as the third compound from the bottom of the table in Column 6 under the code number GF 32.

When employing the active principle of the method of the invention in the form of an acid addition salt, the acid is selected so as to contain an anion which is non-toxic and pharmacologically acceptable, at least in usual therapeutic doses. Representative salts which may be included in this group are the hydrochlorides, hydrobromides, sulfates, acetates, phosphates, nitrates, quinates, tartrates, and maleates. Other acid addition salts are suitable and may be employed if desired. For example, fumaric, benzoic, ascorbic, pamoic, succinic, salicylic, bismethylenesalicylic, propionic, gluconic, malic, malonic, mandelic, cinnamic, citraconic, stearate, palmitic, itaconic, glycolic, benzenesulfonic, and sulfamic acids may also be employed as acid addition salt-forming acids. Organic and inorganic acids are suitable.

Salts with cation exchange resins may also be used, as they provide oral sustained release preparations since the free base or a biologically-absorbent moiety is released from these resin salts slowly and over an extended period of time. These resin salts, therefore, likewise fall within the scope of those utilizable as active principles according to the present invention. Still other pharmaceutically-acceptable salts may be employed if desired, and innumerable such salts will readily present themselves and be obvious to one skilled in the art.

In general, the active principle of the present invention can be conveniently prepared and isolated in conventional manner either in the form of the free base or an acid addition salt thereof. Indication of typical suitable acid addition salts has already been given in the foregoing. While it is preferred to isolate and employ the active principle of the present invention in the form of a solid or crystalline acid addition salt, if for any reason it is desired to employ the active ingredient in the form of the free base, it may be obtained according to conventional procedure, for example, by conducting the reaction for its production in a solvent and thereafter evaporating the solvent to obtain the reaction product as an almost colorless oil, or by dissolving an isolated hydrochloride or other salt in water, neutralizing with a base such as ammonia, ammonium hydroxide, sodium carbonate or other suitable alkaline material, extracting the liberated base with a suitable solvent such as ether or benzene, drying the extract, and evaporating to dryness in vacuo or fractionally distilling. Addition salts may also be made from the free base according to conventional procedure by taking up or dissolving the free base in a suitable solvent and acidifying with the selected acid, the salt of which is desired, which in many cases results in precipitation of the acid addition salt. In other cases the desired salt may be isolated by cooling the solution or by evaporating excess solvent, or in similar known manner for the isolation of acid addition salts. Certain of the acid addition salts may also be isolated directly from the reaction by adding the selected acid to a neutralized solvent solution of the reaction product.

Dosage Forms

Unit dosage forms for use according to the present invention may be of any suitable and/or conventional type. For oral administration, the unit dosage form generally contains about 100 to 300 mg of the active appetite-suppressant compound selected, preferably about 100 mg thereof. For rectal administration in the form of a rectal suppository, the unit dose usually contains about 50 to 600 mg of the active appetite-suppressant compound selected, preferably about 300 mg thereof. As already stated, the appetite-suppressant compound selected is preferably administered together or in conjunction with a pharmaceutically-acceptable carrier.

According to the usual practice of the art, the active appetite-suppressant compound is therefore generally associated with a non-toxic pharmaceutical diluent or carrier which may be either a solid material or a liquid. Bland carriers are preferred for some applications. The composition can take the form of tablets, powders, capsules, liquid solutions, emulsions or suspensions, or other dosage forms which are particularly useful for oral administration. Liquid or semi-liquid diluents may be employed for oral use. Such a medium can be or contain a solvent such as water. The only basic limitations of the liquid diluent used are compatibility and palatability. The compositions can take the form of femoxetine or an acid addition salt thereof admixed with solid diluents and/or tableting adjuvants such as rice starch, corn starch, potato starch, lactose, sacharose, gelatin, talc, stearic acid, magnesium stearate, carboxymethylcellulose, gums such as gum acacia or tragacanth, chicle, agar agar, or the like. Any of the tableting materials used in pharmaceutical practice can be employed where there is no incompatability with the active ingredient or ingredients. The active ingredient can be tableted or otherwise compounded with or without other coactive materials. Alternatively, the active ingredient with or without active adjuvant material can be placed in the usual capsule of absorbable material, such as the usual gelatin capsule, and administered in this form. High concentrations of active ingredient can be employed by utilizing table triturates. In yet another embodiment, the powered active ingredient with adjuvant material can be placed into powder packets. Other examples of compositions in which the active ingredient may be embodied are as follows: the composition can be combined with foods of various kinds; it can be prepared in the form of a laminated or enteric coated tablet for prolonged action; it can be combined with an antacid or analgesic, e.g., aluminum hydroxide gel, calcium carbonate, magnesium oxide or trisilicate, acetylsalicylic acid, phenacetin, propoxyphen, or the like; it can be combined with phenobarbital or other sedative barbiturate or narcotic, for example, codeine or the like; it can be combined with local anesthetics effective in the gastrointestinal tract, such as procaine hydrochloride, novocaine, benzocaine, or the like; it can be combined with a diuretic compound, such as chlorthiazide, hydrochlorthiazide, or the like; or it may be combined with any other adjuvant or bulk-producing material, such as methylcellulose or carboxymethylcellulose, or combinations of the foregoing can be provided. Where the active ingredient is combined with one or more other pharmaceutically-active materials, it is of course necessary that the materials be compatible and that the physiological effect of the active ingredient of the present invention not be adversely affected thereby. Besides the foregoing mentioned forms, the compositions of the invention may also take the form of candies, soft drinks, gums, lozenges, syrups, elixirs, and the like. Reference is made to U.S. Pat. Nos. 1,907,203, 2,196,768, and 2,433,244 for suitable tablet coatings for lamination or enteric coatings; U.S. Pat. No. 2,875,130 for other sustained release type formulations which may be employed; to Remington on Pharmacy for various pharmaceutical formulations and procedures which may be employed; and to the specifications and examples of U.S Pat. Nos. 2,753,288 and 2,881,113 for additional pharmaceutical forms, carriers and types of formulations and combinations in which the active ingredient of this invention may be substituted for the active ingredient of the patents in question. Suppositories or other compositions for rectal administration may be of any suitable or conventional type, for example, having the active ingredient dispersed in an ointment, wax, or polyethylene glycol base, preferably one which melts at or about body temperature, or otherwise in accord with the skill of the art in that particular area of medicine and drug delivery.

The proportion of active ingredient in the compositions of the present invention can be varied. It is only necessary that the selected active ingredient constitute an effective amount, i.e., such that a suitable dosage will be obtained consistent with the dosage form employed. Obviously several unit dosage forms may be administered at about the same time. In terms of percentages, the active ingredient in suitable pharmaceutical compositions which may be employed according to the present invention ordinarily comprise about 0.1 to about 80 weight percent, preferably about 0.5 to about 60 percent, varying because of the form of the composition involved from very low in liquid preparations and bulky tablets, as in combination with antacids or other coactive materials, to quite high in the case of tablets containing a single active appetite-suppressant compound or other solid-dosage forms. With most solid-dosage forms, the percentage is preferably about 10 to 60 percent by weight of the compositions. In the preparation of unit dosage forms, the skill of the art is entirely adequate to provide innumerable unit dosage forms and such will present themselves and will be apparent to anyone skilled in the art upon reading of this disclosure.

Daily Dosages

As already stated, the active appetite-suppressant compound, according to the method of the present invention, is generally administered orally in a daily dosage of about 100 to 1,000 mg, preferably about 400 to 600 mg, and is generally administered rectally in a daily dosage of about 50 to 600 mg. Preferred dosages, as will be understood, vary greatly with the individual, his body weight, his tolerances or intolerances, and must be ascertained by the physician in each case. The amounts given in the foregoing are in accord with clinical experience whereby the desirable anorexigenic and weight-control and/or reduction effects have been obtained over an extended period of treatment, which may be described as long-term treatment, without the development of any anorectic tolerance on the part of the individual treated, such long-term treatment extending over a period of at least eight (8) weeks and even as long as nine (9) months, as will be apparent from an inspection of the clinical trials reported herein.

DETAILED DESCRIPTION OF THE INVENTION

The following preparations and examples in the form of clinical trials are given by way of illustration only and are not to be construed as limiting.

Preparation of Femoxetine Tablets

A representative unit oral dosage form may contain the following:

| | | MG |
|---|---|---|
| 1. | Femoxetine acid addition salt, preferably the hydrochloride. | 100.0 |
| 2. | Lactose | 126.0 |
| 3. | Cellulose (micrystalline) | 54.0 |
| 4. | Polyvidonum (TM-Povidone USP XX) | 10.1 |
| 5. | Glycerol (85 percent) | 4.9 |
| 6. | Magnesium Stearate | 3.2 |
| 7. | Talcum | 34.1 |
| 8. | Saccharine | 78.1 |
| 9. | Titanium Dioxide (CI 77891) | 0.9 |
| 10. | Gelatine | 0.1 |
| 11. | Glucose (Liquid) | 0.6 |
| 12. | Gum Acacia | 4.0 |
| 13. | Eudragit L (TM-Polyacrylate resin) | 3.8 |

Representatively, the method of manufacture of the tablets may be as follows:

Items 1–3 are thoroughly mixed and granulated with a solution of Items 4 and 5 in alcoholic water. The resulting dry granules are mixed with Items 6 and 7. After compression into the form of tablets, each weighing 320 mg, the tablets are sugar-coated with Items 8–12 and, if desired, given an enteric coating with Item 13. Tablets of this composition were employed in the clinical testing, reports of which now follow.

Numerous other unit dosage forms containing an effective anorexigenic amount of femoxetine or a pharmaceutically-acceptable salt thereof, as disclosed elsewhere herein, are prepared and employed with equal facility according to the established skill of the pharmaceutical and medical arts.

CLINICAL TRIAL NO. 1

Design

This investigation by 21 general practitioners was designed as a multi-center double blind group-comparative study of femoxetine* and placebo.

Obese patients with an overweight of 20–60% according to the well-known Natvig scale (Oslo, 1956) were weighed every fortnight during the treatment period of sixteen weeks.

Each participating general practitioner received six (6) boxes of tablets for treatment of six (6) patients. Three (3) boxes contained placebo and the remaining three (3) contained femoxetine tablets.**

*In the reported clinical trials, the product femoxetine was employed in the form of its hydrochloride salt.
**Tablets were prepared as in the foregoing preparation and contained 100 mg of femoxetine hydrochloride.

Dosage

The daily dosage of femoxetine was 100+200 mg for the first week and thereafter 200+200 mg for the rest of the treatment period.

Dietary Advice

A table with caloric values of common food components was delivered to each patient, but dietary restriction with a maximum of total energy intake was not demanded.

Results

1. Patient Material

Twenty-one general practitioners carried out the trial, each treating an average of three to four (3–4) patients.

Forty-four of 74 patients completed the treatment period of 16 weeks. Placebo: 24 out of 35; femoxetine: 20 out of 39.

Only three (3) patients, treated with femoxetine, were withdrawn from the trial due to side effects.

2. Weight Reduction

The weight reduction obtained by the two groups of patients after treatment for sixteen (16) weeks resulted in mean values of weight losses of 2.2 kg and 6.0 kg after sixteen (16) weeks of treatment with placebo and femoxetine, respectively. By use of Student's t-test, the difference between the two groups differs from zero (P-value <0.02).

The time courses of weight reduction obtained by the two patient groups were plotted (weight change vs. time). The resulting graph indicated that further reduction of body weight might be expected if femoxetine treatment were continued for more than 16 weeks.

The distribution of patients according to the degree of weight reduction obtained after treatment with placebo and femoxetine for 16 weeks was plotted (weight change vs. number of patients). The range of weight changes was much smaller with the femoxetine treatment than with the placebo treatment.

Conclusion

Femoxetine, administered in a daily dosage of 400 mg for 16 weeks to obese patients in general practice caused a significant weight reduction, i.e., a mean value weight reduction of 6.0 kg in comparison with a mean value weight reduction of 2.2 kg in placebo patients.

CLINICAL TRIAL NO. 2

Design

In this clinical trial, femoxetine was investigated in thirteen (13) obese women for its weight-reducing effect. The femoxetine was administered in a daily dose of 300 mg for a period of two (2) up to sixteen (16) weeks. Eight (8) of thirteen (13) women undergoing the treatment lost weight, the amount of weight loss being 0.2 to 8.5 kg, with the mean weight loss being 2.8 kg.

No correlation between degree of 5-HT reduction and weight loss could be ascertained.

Patients and Methods

Femoxetine was administered to obese women in a daily dose of 300 mg (100 mg in the morning, 200 mg in the afternoon) in an open investigation.

They were all weighed at intervals of one (1) week for the first month and then at visits every fortnight. At these visits, blood samples for determination of femoxetine in plasma and 5-HT in whole blood were withdrawn. The blood samples were taken in the morning fourteen (14) to sixteen (16) hours after the last dose. Concentrations of femoxetine were determined by gas-chromatography (Bechgaard and Lund, J. Chromatogr. 133, 147–152 (1977); Bechgaard et al., Anal. Chim. Acta: 99: 189–192 (1978). The 5-HT determinations were performed using a modification of the method by Squires (Journal of Neurochemistry 1975, 24, 47).

Women who desired medicinal treatment of adipositas and who were without endochrinological or other serious diseases were allowed to enter the pilot trial. Thirteen (13) women in the age group from 49 to 69 years started the treatment, which was planned to last sixteen (16) weeks. Apart from adipositas, all except two (2) patients were without concurrent somatic disease. One woman suffered from diabetes mellitus, and another had a moderate hypertension.

All had been obese for many years and had attempted dieting under medical supervision on previous occasions without success.

The mean of the weight of these patients was, at the beginning of the study, 83.2 kg. The degree of adipositas was described by the percentage of the weight above the ideal weight (Natvig, 1956). These percentages varied from sixteen (16) to 111 (mean 41). The women were not told to take a restricted diet during the treatment period.

Results

Eight of thirteen (13) women lost weight in amounts of 0.2 to 8.5 kg (mean 2.8 kg). The weight of one patient was unchanged and four (4) patients gained from 0.4 to 2.0 kg. The changes in body weight during the treatment period for patients treated for more than eight (8) weeks showed that, in at least four (4) patients, weight losses continued for ten (10) to sixteen (16) weeks.

The 5-HT concentration in whole blood was reduced from a mean value of 0.14 to 0.05 $\mu$g/ml at the end of three (3) weeks' treatment. After treatment for sixteen (16) weeks, the 5-HT concentration was still 0.05 $\mu$g/ml. No correlation between the degree of 5-HT reduction and weight loss was obtained. No correlation between the degree of obesity and weight reduction was obtained.

Side Effects

Side effects were recorded in four (4) patients. Three (3) patients recorded dry mouth. The cases were all mild and transient and disappeared with continued treatment. One patient discontinued treatment because of dyspepsia initially leading to constipation after treatment for three (3) weeks. Four (4) patients mentioned an anoretic effect initially.

Dropouts

Five (5) women stopped the treatment for reasons not related to femoxetine. Two (2) of these failed to appear, and one (1) patient wanted to stop the treatment because of no weight reduction after seven (7) weeks. One patient was troublesome and treatment was stopped by the doctor for practical reasons. The last patient was withdrawn from femoxetine treatment because of medicinal treatment of her untreated hypertension.

Femoxetine

Generally, the steady-state plasma concentrations of femoxetine were below the analytical limit (5 ng/ml). Only two (2) women had measurable values and the highest steady-state concentration obtained was 30 ng/ml.

Discussion

This study indicates that femoxetine is effective in reducing the weight of women with refractory obesity.

The loss of weight was sustained as long as the drug was given and the side effects were mild and transient.

CLINICAL TRIAL NO. 3

In a similar study, involving two (2) obese females treated with 600 mg of femoxetine daily, the mean weight reduction was 3 kg after two (2) weeks, 4.5 kg after four (4) weeks, 7.5 kg after six (6) weeks, 11 kg after ten (10) weeks, 13 kg after thirteen (13) weeks, 14 kg after twenty (20) weeks, 16 kg after twenty-eight (28) weeks, 19 kg after thirty-six (36) weeks, and 22.8 kg after forty-four (44) weeks. (One patient lost 18 kg, the other 27.6 kg, for a mean weight loss of 22.8 kg).

CLINICAL TRIAL NO. 4 (Appetite and weight control in chronically obese patients)

Design

The trial was designed as a double-blind group-comparative study of femoxetine and placebo in two clinics.

The body weight of obese patients was measured before the patients started the medication, after two (2) weeks of treatment, and subsequently every third week during the total treatment period of seventeen (17) weeks.

The quantity and the composition of the food were estimated by these patients and by dietary assistants before the treatment started and twice during the study period.

Free Dietary Allowances

The patients were on free dietary allowances without any limitation or selection on any food item.

The purpose of the no dietary restriction at all was to look for weight-reduction in combination with a spontaneous alteration of the components of food intake during femoxetine treatment.

Inclusion Criteria

Patients which according to Natvig's scale of ideal weight had an overweight of 20–95% and were in the age between 20 and 70 years (inclusive) entered the trial.

The patients were either routinely referred to the outpatient clinic at the two departments or they were already familiar with the clinics from earlier attempts at weight reduction by use of anorectic drugs, dietary advice, or dietary restrictions.

Dosage

The daily dosage of placebo and femoxetine tablets of 100 mg was one (1) tablet three (3) times daily for two (2) weeks and thereafter two (2) tablets three (3) times daily for the remainder of the treatment period. No other medication was allowed during the study.

Quantity and Quality of Food

A careful recording of all food items consumed daily for one (1) week was performed by each subject before and twice during the four (4) month medication period. The daily food records were further analyzed and coded by four (4) professional research dieticians for entry into a computer program (CAMP-system, Danish Hospital Institute) containing information regarding the contents of energy, protein, carbohydrate and fat in 600 different food items of present Danish menus.

Results

1. Patient Material

Seventy-three (73) of 111 patients completed the treatment period of seventeen (17) weeks.

Four (4) patients were withdrawn from the trial due to side effects, and nineteen (19) patients failed to appear or withdrew in default of effect. These patients have been excluded from the analysis together with other patients according to the exclusion criteria previously stated for the trial plan.

The distribution of the patients according to sex, age, overweight and clinic was recorded in tabular form. The distribution showed that the two (2) groups can be regarded as comparable.

Forty-seven (47) of 73 patients, included in the analysis, were referred to the two clinics for the first time when they entered the trial. The remaining 26 patients had all made earlier attempts at weight reduction at the clinics with the result of weight change in the range of $-12$ kg to $+7$ kg for the period of three (3) months just previous to this study.

2. Weight Change

After treatment with femoxetine for seventeen (17) weeks, the body weight was unchanged. The mean value of weight change was 0.0 kg, the range being $-9.4$ to $+7.8$ kg. The corresponding result for the placebo group was a weight gain averaging 1.6 kg. No essential difference existed between the results obtained from the two (2) clinics.

The time course of the weight changes obtained by the two (2) treatment groups was charted. No significant weight reduction was obtained at the beginning of the treatment or afterward at any time during the treatment period.

The distribution of patients according to the degree of weight change obtained after seventeen (17) weeks of treatment was charted and showed a more even distribution and less weight gain for the femoxetine-treated patients.

Eleven (11) patients lost more than 3.0 kg of their body weight during femoxetine administration, whereas only four (4) patients on placebo realized such a weight reduction. A survey on those eleven (11) femoxetine patients was carried out and indicates that no special distribution according to age or degree of overweight is apparent.

3. Energy Intake and Intake of Protein, Fat and Carbohydrate

During the study period, no changes of food intake were registered. The total energy intake and the amount of protein, fat and carbohydrate consumed for one (1) week were thus approximately the same before and during the treatment.

Conclusion

Just previous to this study, one-third ($\frac{1}{3}$) of the patients were familiar with the clinic from earlier attempts at weight reduction with dietary restriction, often in combination with drug-supported therapy. Therefore, a subsequent drug-trial with free dietary allowances could only with difficulty cause reduction of body weight for such patients. However, appetite and weight control was realized.

The purpose of this study design, however, which did not include any dietary restrictions, was mainly to look for weight reduction and/or control in combination with possible spontaneous alteration of the components of food intake during femoxetine treatment. An increase in the amount of protein during an unchanged or reduced total energy intake might have been expected. No alteration of the three (3) components of energy or total energy intake was observed during the study, however, for which reason reduction of body weight was not observed either.

CLINICAL TRIAL NO. 5

Femoxetine was administered in a daily dose of 300–400 mg to a total of twenty-one (21) outpatients who were overweight by twenty percent (20%). The mean degree of overweight was forty-one percent (41%). Sixteen (16) patients completed twelve (12) weeks of treatment, whereas five (5) patients discontinued after partial treatment for over a period of seven (7) to nine (9) weeks, all for reasons not related to the drug therapy. The younger patients, up to an age of 45 years, compared to the group above 45 years of age, was characterized by a higher level of physical activity combined with a higher intake of energy, as would be expected.

Twenty (20) patients lost weight, the mean weight reduction being 3.1 kg. The larger weight reduction was observed in the younger group of patients. For the sixteen (16) outpatients who completed the full twelve (12) weeks of outpatient treatment, the average weight reduction in the younger group was 4.8 kg (n=8, s.d.=2.5), whereas the corresponding value for the older group was 2.2 kg (n=8, s.d.=1.2). This difference in weight reduction between the two age groups was significant, the Student's t-test for unpaired values giving a P-value of 0.02. The time course of weight reduction for each of the two age groups was charted and showed certain variations. At all points in the trials, the weight change in the group under 45 years of age was greater than in the group which was over 45 years of age. For example, at three (3) weeks, the average weight reduction in the over 45 year group was 1.5 kg, whereas in the under 45 year group it was 2.5 kg. At eight (8) weeks, the corresponding figures were 2 kg and 3.5 kg. At ten (10) weeks, the corresponding figures were somewhat more than 2 kg and 4 kg, and at the end of twelve (12) weeks, the corresponding figures represented weight losses of 2.5 and nearly 5 kg in the respective age groups.

The protocol for the clinical trial involved advice to the patients, who were requested not to diet and who received no advice to change their eating habits, but who were told to eat the same food as usual and let hunger and satiety decide the size of the meal. Only a few side effects were reported. Three (3) patients complained of dry mouth and one of nausea, but the complaints were all mild and the symptoms disappeared during further treatment. Two (2) patients reported remission of a headache. Laboratory investigations of blood picture, liver and kidney function did not show any significant changes during the treatment. ECG monitor showed a normal pattern before, during, and after the treatment for all patients involved.

In this trial, the maximal reduction of 5-HT concentration in whole blood, to a value of 0.07 µg/ml, was obtained after a treatment period of three (3) weeks. Four (4) weeks after termination of the treatment, the mean of the 5-HT concentration was 0.14 µg/ml, indicating a return to a normal 5-HT level. All steady-state concentrations of femoxetine were very low. Only three (3) patients had plasma concentrations above the analytical limit of 5 ng/ml, and the steady-state concentrations for these patients varied between 6 and 20 ng/ml. Regardless of the very low steady-state concentration of femoxetine, 5-HT in whole blood was strongly reduced during the treatment, indicating an inhibition of 5-HT uptake into blood platelets at very low concentrations of femoxetine. No CNS-stimulant effect was observed during the clinical trials.

The results of the clinical trial evidenced that femoxetine is useful in assisting with appetite and weight control and reduction in obese human patients over a twelve-week treatment period.

CLINICAL TRIAL NO. 6

Design

A follow-up study has been undertaken on obese patients who previously participated in a double-blind group-comparative study of femoxetine and placebo. The results of that study, which was performed at two outpatient clinics in Copenhagen, have been reported heretofore under the heading "CLINICAL TRIAL NO. 4".

Methods

After termination of treatment for seventeen (17) weeks in a double-blind study, all patients at one of the two clinics were invited to take or continue femoxetine treatment.

Contrary to the instructions with free dietary allowances in the treatment period just previous to this study, the patients were now given dietary advice. They were told about the advantages of weight-reduction programs which combined dietary restriction to about 5000 kilojoules and anorectic treatment. However, no attempt was made to otherwise determine or control whether any dietary restriction was followed.

The daily dosage of femoxetine was 600 mg. The patients visited the clinic once a month for weight and laboratory control. The patients were offered femoxetine for a maximum period of six (6) months.

Results

Twenty-eight (28) of a total number of thirty-five (35) patients, who completed the double-blind trial, were in treatment with femoxetine for more than six (6) weeks. Ten (10) of the patients had just previously been in treatment with femoxetine for seventeen (17) weeks, whereas eighteen (18) patients had received placebo.

The average weight-reduction obtained was 5.2 kg (SD=5.5, n=28) after an average treatment period of sixteen (16) weeks.

For the patients previously treated with femoxetine the average weight reduction was 2.1 kg, whereas the corresponding value for patients previously treated with placebo was 6.9 kg.

The degree of weight reduction observed together with the duration of treatment were tabulated and charted, and confirmed the results just stated.

For six (6) patients, a weight reduction of more than 10 kg was observed. They lost an average of 13.6 kg during trials having a mean duration of twenty-one (21) weeks.

Eleven (11) patients received femoxetine for five (5) months. By adding their seventeen (17)-week treatment period in the double-blind study just previous to this study, they were under treatment for nine (9) months. The time course of weight change with an overall average weight reduction of 10 kg after nine (9) months of treatment was charted and dramatically illustrated this remarkable weight loss in eleven (11) of the patients subjected to trial.

Discussion

During a double-blind study with free dietary allowances, neither the femoxetine nor the placebo group obtained significant weight reductions. The patients treated with femoxetine lost 0.5 kg on an average, whereas the placebo group showed a weight gain of 1.1 kg.

In the open follow-up study with femoxetine treatment and dietary advice, a significant weight reduction of 5.2 kg was observed. The highest degree of weight loss was obtained by patients previously treated with placebo.

In retrospective comparison with similarly designed trials in obese patients receiving chlorophentermine, phenmetrazine and fenfluramine, fenfluramine was the only drug to maintain effective weight loss up to twelve (12) weeks[1], although there are reports of tolerance to fenfluramine developing within weven (7) weeks of beginning treatment[2]. The results in this study indicate that femoxetine still produces anorectic effects after eight (8) months of treatment.

It is further concluded that femoxetine is better given together with dietary advice than alone, although it is also effective in those patients who are on free diet.

[1] Pinder, R. M. et al.: Fenfluramine: A review of its pharmacological properties and therapeutic efficacy on obesity. Drugs 1975, 10 (4), 241-323.

[2] Stunkard, A. et al.: Fenfluramine in the treatment of obesity. Lancet 1973, 1, 503.

RECTAL ADMINISTRATION

In suitable biopharmaceutical studies, it was determined that a unit size suppository containing 300 mg of femoxetine administered rectally twice daily is effective in producing plasma concentrations equivalent to those produced using 600 mg of femoxetine orally, an effective daily dose. Wider ranges may be employed. Suppositories containing as low as fifty mg of femoxetine may be used, and 600 mg is a highly effective daily rectal dose, preferably broken down into smaller unit dosages. The suppositories tested in these studies contained the femoxetine uniformly dispersed in the usual meltable suppository base.

From the foregoing, it will be apparent that a novel method for the long-term treatment of human patients, especially obese human patients, for purposes of appetite and weight control and reduction, and whereby all of the additional objects of the invention may be accomplished, has been provided by the present invention.

It is to be understood that the invention is not to be limited to the exact details of operation or exact compounds, compositions, methods, or procedures shown and described, as obvious modifications and equivalents will be apparent to one skilled in the art.

We claim:

1. The method of reducing appetite to obtain weight control and reduction in an obese human patient which comprises the step of orally or rectally administering to the said patient an appetite suppressing amount of a compound selected from the group consisting of femoxetine and a pharmaceutically-acceptable salt thereof over a period of at least eight (8) weeks.

2. The method of claim 1, wherein the appetite-suppressant compound is administered together with a pharmaceutically-acceptable carrier.

3. The method of claim 1, wherein the appetite-suppressant compound is administered orally in a daily dosage of about 100 to 1,000 mg.

4. The method of claim 3, wherein the appetite-suppressant compound is administered orally in a daily dosage of about 400 to 600 mg.

5. The method of claim 1, wherein the appetite-suppressant compound is administered orally in an oral unit dosage form containing about 100 to 300 mg thereof.

6. The method of claim 5, wherein the appetite-suppressant compound is administered orally in an oral unit dosage form containing about 100 mg thereof.

7. The method of claim 1, wherein the appetite-suppressant compound is administered rectally in a daily dosage of about 50 to 600 mg.

8. The method of claim 7, wherein the appetite-suppressant compound is administered in the form of a rectal suppository containing about 50 to 600 mg thereof.

9. The method of claim 8, wherein the appetite-suppressant compound is administered in the form of a rectal suppository containing about 300 mg of the active ingredient.

10. The method of claim 1, wherein the appetite-suppressant compound is administered over a period in excess of eight (8) weeks.

11. The method of claim 10, wherein the appetite-suppressant compound is administered over a period of at least twelve (12) weeks.

12. The method of claim 1, wherein the appetite-suppressant compound is administered daily over a period in excess of eight (8) weeks.

13. The method of claim 12, wherein the appetite-suppressant compound is administered daily over a period of at least twelve (12) weeks.

14. The method of claim 12, wherein the appetite-suppressant compound is a femoxetine pharmaceutically-acceptable acid addition salt which is orally-administered in a daily dosage of 100 to 1,000 mg in the form of a tablet containing about 100 to 300 mg thereof.

15. The method of claim 14, wherein the compound is femoxetine hydrochloride.

16. The method of reducing appetite to obtain weight control and reduction in an obese human patient on a long-term basis without the development of anorectic tolerance on the part of the patient which comprises the step of orally administering to the said patient an appetite suppressing amount of a compound selected from the group consisting of femoxetine and a pharmaceutically-acceptable salt thereof over an extended period, the daily dosage being about 100 to 1,000 mg in a unit-dosage form containing about 100 to 300 mg thereof.

* * * * *

UNITED STATES PATENT AND TRADEMARK OFFICE
CERTIFICATE OF CORRECTION

PATENT NO. : 4,442,113

DATED : April 10, 1984

INVENTOR(S) : Joergen B. Lassen, Birte K. Skrumsager and Joergen A. Christensen

It is certified that error appears in the above—identified patent and that said Letters Patent is hereby corrected as shown below:

Col. 2, line 37; "desamphetamine," should read -- dexamphetamine, --
Col. 6, line 44; "table" should read -- tablet --
Col. 7, line 42; "compositions." should read -- composition. --
Col. 9, line 15; "reduction" should read -- reductions --
Col. 10, line 4; "endochrinological" should read -- endocrinological --
Col. 15, line 23; "weven" should read -- seven --

Signed and Sealed this

Twentieth Day of November 1984

[SEAL]

Attest:

GERALD J. MOSSINGHOFF

Attesting Officer

Commissioner of Patents and Trademarks